US008820140B2

(12) United States Patent
Puget et al.

(10) Patent No.: US 8,820,140 B2
(45) Date of Patent: Sep. 2, 2014

(54) SYSTEM FOR ANALYZING A GAS MIXTURE INCLUDING AT LEAST ONE CHROMATOGRAPHY COLUMN

(75) Inventors: Pierre Puget, Saint Ismier (FR); Edward B. Myers, Burbank, CA (US); Michael L. Roukes, Pasadena, CA (US)

(73) Assignees: Commissariat à l'énergie atomique et aux énergies alternatives, Paris (FR); California Institute of Technology, Pasadena, CA (US)

( * ) Notice: Subject to any disclaimer, the term of this patent is extended or adjusted under 35 U.S.C. 154(b) by 0 days.

(21) Appl. No.: 13/702,727

(22) PCT Filed: Jun. 6, 2011

(86) PCT No.: PCT/EP2011/059304
§ 371 (c)(1),
(2), (4) Date: Feb. 7, 2013

(87) PCT Pub. No.: WO2011/154362
PCT Pub. Date: Dec. 15, 2011

(65) Prior Publication Data
US 2013/0125621 A1 May 23, 2013

Related U.S. Application Data

(60) Provisional application No. 61/352,241, filed on Jun. 7, 2010.

(51) Int. Cl.
*G01N 30/78* (2006.01)
(52) U.S. Cl.
USPC .......................................... 73/23.39
(58) Field of Classification Search
USPC ........................................... 73/23.35
See application file for complete search history.

(56) References Cited

U.S. PATENT DOCUMENTS 2,920,478 A * 1/1960 Golay ........................ 73/23.35
3,204,448 A * 9/1965 Bevan et al. ................. 73/23.4
(Continued)

FOREIGN PATENT DOCUMENTS

DE 197 52 909 A1 6/1999

OTHER PUBLICATIONS

Lee, C., Sharma, R., Radadia, Adarsh D., Masel, Richard I. and Strano, Michael S. (2008), On-Chip Micro Gas Chromatograph Enabled by a Noncovalently Functionalized Single-Walled Carbon Nanotube Sensor Array. Angew. Chem. Int. Ed., 47: 5018-5021. doi: 10.1002/anie.200704501.*
U.S. Appl. No. 13/702,790, filed Feb. 2, 2013, Ernst et al.

(Continued)

*Primary Examiner* — Hezron E Williams
*Assistant Examiner* — Mark A Shabman
(74) *Attorney, Agent, or Firm* — Oblon, Spivak, McClelland, Maier & Neustadt, L.L.P.

(57) ABSTRACT

A system for analyzing a gas mixture, including at least one chromatography column, a mechanism injecting the mixture into the column, and a mechanism detecting compound(s) forming the gas mixture, the detection mechanism including at least one detector of nanosensor type of an outlet of the column and a detector of nanosensor type in the column, capable of detecting passage of the compounds. It is then possible to determine the velocity of each of the compounds within the system.

17 Claims, 6 Drawing Sheets

(56) References Cited

U.S. PATENT DOCUMENTS

| | | | |
|---|---|---|---|
| 3,486,304 A * | 12/1969 | Jentzsch | 96/104 |
| 5,116,495 A * | 5/1992 | Prohaska | 210/198.2 |
| 5,641,893 A * | 6/1997 | Penn et al. | 73/61.53 |
| 6,581,441 B1 * | 6/2003 | Paul | 73/61.52 |
| 6,732,567 B2 * | 5/2004 | Briscoe et al. | 73/23.39 |
| 2003/0109054 A1 * | 6/2003 | Sacks et al. | 436/161 |
| 2006/0193748 A1 * | 8/2006 | Tai et al. | 422/70 |
| 2007/0256474 A1 * | 11/2007 | Paakkanen et al. | 73/23.37 |
| 2009/0084496 A1 * | 4/2009 | Fonverne et al. | 156/292 |
| 2009/0272270 A1 * | 11/2009 | McGill et al. | 96/101 |
| 2009/0320991 A1 * | 12/2009 | Boyle et al. | 156/151 |
| 2013/0144542 A1 | 6/2013 | Ernst et al. | |

OTHER PUBLICATIONS

International Preliminary Report on Patentability, dated Oct. 12, 2012 for International application No. PCT/EP2011/059304.

International Search Report, International application No. PCT/EP2011/059304, Form PCT/ISA/210 (second sheet) Sep. 9, 2012.

Joshua J. Whiting, et al., "High-Speed Two-Dimensional Gas Chromatography Using Microfabricated GC Columns Combined With Nanoelectromechanical Mass Sensors", Transducers 2009, Denver, CO, USA, Jun. 21-25, 2009.

Jianhai Sun, et al., "A High Resolution MEMS Based Gas Chromatography Column for the Analysis of Benzene and Toluene Gaseous Mixtures", Sensors and Actuators 8-141 (2009) 431-435.

Jean-Marie D. Dimandja "Comprehensive 2-D GC provides high-performance separations in terms of selectivity, sensitivity, speed, and structure." Analytical Chemistry, May 1, 2004, pp. 167 A-174 A.

Bradley C. Kaanta, et al. "A monolithically fabricated gas chromatography separation column with an integrated high sensitivity thermal conductivity detector" Journal of Micromechanics and Mircoengineering, 2010, pp. 1-6.

Patrick R. Lewis, et al. "Recent Advancements in the Gas-Phase MicroChemLab" IEEE Sensors Journal, vol. 6, No. 3, Jun. 2006, Jun. 2006, pp. 784-795.

U.S. Appl. No. 13/702,226, filed Apr. 17, 2013, Ernst et al.

* cited by examiner

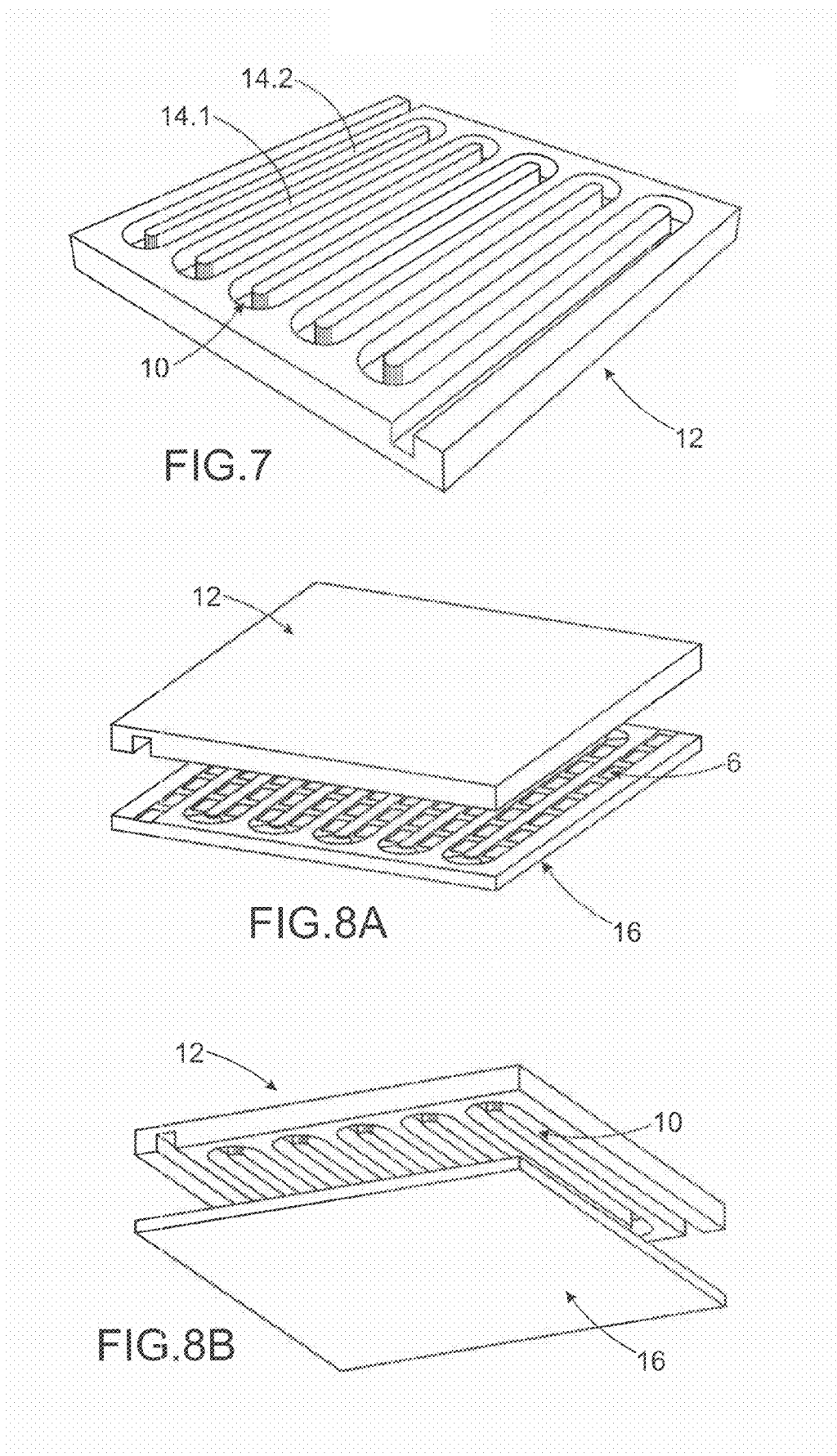

SYSTEM FOR ANALYZING A GAS MIXTURE INCLUDING AT LEAST ONE CHROMATOGRAPHY COLUMN

TECHNICAL FIELD AND PRIOR ART

The present invention relates to a system for analyzing a gas mixture comprising at least one chromatography column in order to determine the constituents of the mixture. The present invention more particularly relates to analysis systems including one or more chromatography columns of the microcapillary type, for example formed with a hollow tube having a diameter comprised between 10 µm and a few hundred micrometers, or of the macrocapillary type with a diameter comprised between about 500 µm and a few millimeters, and the length of which varies between several centimeters to several meters.

For example the question is of detecting the presence of a particular gas in a mixture at a given concentration threshold.

The applications of this type of detection system are numerous, and notably in the field of air quality monitoring, food and agriculture monitoring, process and safety monitoring.

Such a detection system includes a gas chromatography column and a detector at the outlet of the column. A pre-concentrator or injection system may be provided at the inlet of the column.

The chromatography column is intended for separating the different constituents of the mixture so that the latter exit the column at different instants and are detected successively.

This separation within the column is obtained by the presence of a stationary phase covering the inside of the column and having more or less affinity with the constituents; the constituents then move at different rates.

In present systems applying a chromatography column, it is assumed that the velocity of each constituent is constant in the column. Now, this assumption is only true if the thickness of the stationary phase is constant. But obtaining such a constant thickness imposes technological constraints, the price cost of which is high, on the methods for manufacturing columns.

Moreover, with the systems of the state of the art, a second mixture cannot be injected into the column before all the constituents of the first mixture have exited the column. Indeed, as we have shown, the displacement velocity in the column depends on the affinity of a constituent with the stationary phase, therefore it may happen that a constituent of the second mixture exits the column before one or more constituents of the first mixture, or is superposed to one of them. It is then impossible to determine whether this constituent belongs to the first or to the second mixture. This requirement of injecting a new mixture when all the constituents of the previous mixture have exited the column may be a great penalty for example when certain constituents are very slow in exiting the column. The rate of the analyses is then low.

In the case of particularly complex mixtures, for example in the field of petrochemistry, a single column is not sufficient for separating all the components. Indeed, for a given stationary phase, several compounds are likely to have the same affinity with this stationary phase. Two columns connected in series are then used having different stationary phases. Each compound is characterized by a pair of affinities with both columns. The mixture crosses the first column and then the second column, each component being separated in the first column and then in the second column. In order to know the affinity pair with each column, both transit times have to be known in each of the columns for each compound. For each compound, i.e. each exiting peak from the second column, the exit instant from this second column and the introduction instant of the sample into the first column are known without any difficulty. On the other hand, it is more difficult to know the instant of passing from the first to the second column. Knowing this instant is required in order to estimate the transfer rates in each column. Indeed, since compounds may "overtake" each other in the second column, therefore not exit from the second column in the same order, it is then not known without any ambiguity how to establish the correspondence between a peak which transits between two columns and a peak which exits a few instants latter from the second column. One of the means used for solving this ambiguity is to modulate the flow rates in the columns with a relatively complex system comprising valves and/or thermal control. Such a system is described in document Dimandja, *J.M.D., GC×GC. Analytical Chemistry*, 2004. 76(9): p. 167A-174A.

Therefore an object of the present invention is to provide a detection system having lesser manufacturing constraints than those of the systems of the state of the art.

It is also an object of the present invention to provide an analysis system applying one or more chromatography columns with which the rate of the analyses of the samples may be increased as compared with the systems of the state of the art and allowing s simplified analysis of the complex samples.

DISCUSSION OF THE INVENTION

The objects stated earlier are achieved by an analysis system including a gas chromatography column and means for detecting components separated within the column, the detection means being located in at least two different points on the flow path of the mixture to be analyzed, so that it is possible to determine the displacement rate of the constituent within the column. For example, the detection means include a detector positioned at the outlet of the column and another detector positioned upstream, at the inlet or within the column. Thus, the velocity of each constituent of the samples may be estimated in a more accurate way, in particular when the velocity of the constituent is not strictly constant along the column. With this it is possible to lower the technological constraints for manufacturing the column.

Moreover, by means of the system according to the invention, a second sample may be introduced before all the constituents of the first sample have exited. Depending on the complexity of the samples, characterized by the number of constituents and of corresponding peaks in the column, a sufficient number of detectors may be available for tracking each constituent and detecting the constituents of the second sample for which the velocity is greater than that of the constituents of the first sample, so that there is then no longer any uncertainty. For samples of arbitrary complexity, it is sufficient to position the detectors with a density such that their spacing is less than the distance corresponding to the half-width of a peak. In order to determine this half-width, a peak corresponding to the solvent or more generally to a constituent not having any or only very little affinity with the stationary phase, will preferably be selected.

Further, the application of several columns, notably of several columns having different stationary phases and which are connected in series, is simplified, since it is no longer necessary to handle the displacement of the different constituents relatively to each other.

In other words, according to the invention, the velocity is used in order to characterize the compounds in the column and no longer only the detection peak provided by the detector at the outlet of the column like in the systems of the state of the art.

In a particularly advantageous way, MEMS type detectors or sensors are used, and still more advantageously detectors of the NEMS type, the dimensions of which allow their integration into the wall of a column, the width of the section of which is of a few tens of micrometers. Further, the NEMS detectors are generally more sensitive than the MEMS detectors.

Advantageously, provision is made for juxtaposing the detectors along the chromatography column, with which it is possible to have specific knowledge on the variation of the velocity of each compound in the column.

The detectors for example are gravimetric microsensors or nanosensors. These may also be conductimetric detectors with a support in nanotubes, for example carbon nanotubes. Other detectors having compatible characteristics in terms of size, sensitivity, response time, may also be contemplated.

The subject-matter of the present invention is then mainly a system for analyzing a gas mixture, including at least one chromatography column, means for injecting said mixture into said column, and means for detecting the compound(s) forming the gas mixture, the detection means being capable of detecting the compounds in at least two locations between the inlet and the outlet of the column, including the inlet and the outlet of the column.

For example, the detection means include at least one detector at the outlet of the column and at least one detector at the inlet and/or in the column.

Advantageously, the detection means include at least one detector at the outlet of the column and at least one detector in the column, more particularly at least one detector is integrated into the wall of the chromatography column.

Preferably, the system according to the invention includes a network of detectors distributed between the inlet and the outlet of the column, along the column.

Advantageously, the spacing between two consecutive detectors is less than or equal to the half-width of a peak.

Advantageously, the column includes a sufficient number of detectors so that each constituent is "seen" at any instant by at least two detectors.

In an embodiment, the system according to the invention includes at least two columns connected in series, the second downstream column including at least two detectors, a detector at the inlet and a detector at the outlet.

The first upstream column may also include a detector positioned at the outlet of the latter. It is well understood that the first column may include a plurality of detectors.

For example, the detectors are gravimetric sensors. In the case when the column(s) is(are) of the microcapillary or macrocapillary type, the detectors are NEMS sensors. The detectors for example have a useful surface area comprised between 100 nm$^2$ and a few µm$^2$.

The detectors may be functionalized by depositing a layer of adsorbing material; the adsorbing material deposited on the detectors may be identical with that of the stationary phase of the column.

The column is for example made by etching a groove in a substrate on the one hand, and by closing said groove with a plate on the other hand. The detectors may be made in the groove or on the plate according to a pattern corresponding to the shape of the groove.

The subject-matter of the present invention is also a method for analyzing samples applying a system according to the present invention, including the steps of:
sequential injection of samples into the column,
detection of the peaks of the constituents of said mixtures,
establishment of trajectory maps of each of the constituents of the mixture, with which the local velocity of each of said constituents may be determined between two successive detectors.

Advantageously, the time between two injections is less than the time for transporting the slowest constituent of the first injection, or even less than the time for transporting the gas solvent.

SHORT DESCRIPTION OF THE DRAWINGS

The present invention will be better understood by means of the description which follows and of the appended drawings wherein:

FIGS. 1A and 1B are schematic illustrations of exemplary embodiments of an analysis system according to the present invention, FIG. 2A is a graphic illustration of a space-time concentration map of the compounds, obtained by means of the analysis systems of FIGS. 1A and 1B in the case when the stationary phase has uniform characteristics along the column, FIG. 2B is a graphic illustration of a space-time concentration map of the compounds, obtained by means of the analysis systems of FIGS. 1A and 1B in the case when the stationary phase has variable characteristics along the column, FIG. 3 is a graphic illustration of a space-time concentration map of the compounds of two successive samples obtained by means of the analysis systems of FIGS. 1A and 1B, FIG. 4A is a schematic illustration of an analysis system according to the present invention including two chromatography columns connected in series, FIG. 4B is a schematic illustration of a space-time concentration map of the compounds, obtained by means of the analysis system of FIG. 4A, FIG. 4C is a chromatography map corresponding to the map of FIG. 4B, FIG. 5A is a graphic illustration of a space-time concentration map of the compounds, obtained by means of the analysis system of FIG. 4A, the compounds having different affinities with the stationary phases as compared with those of the map 4B, FIG. 5B is a chromatography map corresponding to the map of FIG. 5A, FIGS. 6A and 6B are partial top and longitudinal sectional views respectively of a substrate including a spiral-shaped column which may be applied in a system according to the present invention, FIG. 7 is a perspective view of a substrate provided with a column forming to-and-fro paths which may be applied in the present invention, FIGS. 8A and 8B are perspective views of a system according to the present invention, wherein the sensors are formed on the cover;

DETAILED DISCUSSION OF PARTICULAR EMBODIMENTS

In the following description, <<sample>> refers to the gas mixture of compounds which one wishes to analyze.

The terms of "compound", "constituent", "component", <<analyte>> all refer to a solute dissolved in a carrier gas, the latter for example being air.

Figure 1A:
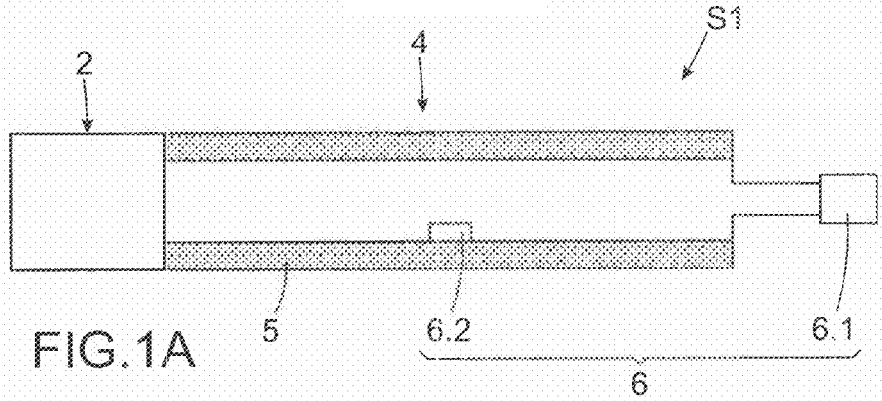

In FIG. 1A, a schematic illustration of an exemplary embodiment of an analysis system S1 according to the present invention may be seen, including injection means 2, a chromatography column 4 and detection means 6.

With the injection means 2 it is possible to introduce the sample to be analyzed and make it volatile. This is for example a volume of air to be analyzed, sampled in a room or a vehicle, the outlet of a pre-concentrator based on solid phase extraction (SPE) or of a thermodesorber, or else a liquid sample (for example a petrochemistry extract, an essential oil) dissolved in an organic solvent. The latter are well-known to one skilled in the art, they will not be described in detail.

The chromatography column 4 is formed by a tube of the microcapillary type for example having a diameter comprised between 10 μm and a few hundred micrometers or of the macrocapillary type, the diameter being comprised between 500 μm and a few millimeters. The length is for example comprised between 0.5 m and a few meters.

The inner surface of the tube is covered with a thin film of material called a stationary phase 5. Deposition of such a material may be carried out with any type of technique known to one skilled in the art. The material of the stationary phase may for example be a polymer, such as polyethylene glycol or polydimethylsiloxane. This material may also be a solid, a gel sol, or a liquid.

The different molecules of the injected sample will be separated according to their affinities with the stationary phase, certain molecules being more slowed down than other ones, which will allow the measurement of the signal emitted by the different molecules and give the possibility of identifying them.

For a given column, a compound is defined by a retention coefficient or factor k. This retention factor corresponds to the ratio between the compound mass in the mobile phase over the compound mass in the stationary phase. This is also the ratio between:

the difference of the respective transit times of the compound and of the solvent,
and the transit time of the solvent (which does not interact with the column) in the column.

A compound having a strong retention factor corresponds to a compound which is strongly slowed down, having strong affinity with the stationary phase of the column.

According to the present invention, the gas detection means 6 allow detection of different compounds in at least two different locations of the analysis system. The detection means include at least two detectors positioned in various ways.

In the illustrated example, a detector 6.1 is positioned at the outlet of the column 4 and a detector 6.2 is positioned in the column, more particularly in the wall of the column 4.

Alternatively, one of them may be positioned at the outlet and the other one may be positioned at the inlet.

By the presence of said at least two gas detectors, it is possible to track the displacement of the solute within the column and to more specifically estimate the instantaneous velocity.

Figure 1B:
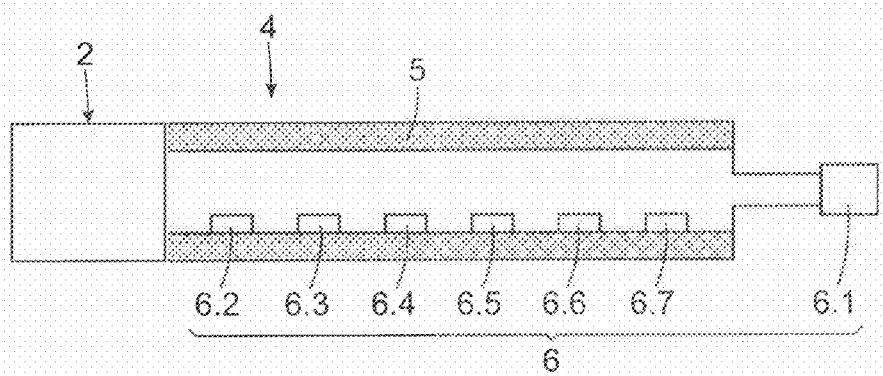

In a particularly advantageous way, the detection means 6 are formed by a network of detectors positioned from the inlet of the column to the outlet of the column. In FIG. 1B, a network of six detectors 6.2 to 6.7 positioned along the column and a detector 6.1 at the outlet of the latter may be seen. The network includes at least a sufficient number of detectors regularly spaced out so that their spacing is less than half the width of a peak. For a given column, the average value of a peak may be estimated by the "height equivalent of a theoretical plate". In practice, it is advantageous to have detectors spaced out by about one millimeter, i.e. about 1,000 for a column of one meter.

The detectors are selected so that their size allows them to be positioned inside the column. In the case of a chromatography microcolumn, the typical section of such a microcolumn has a width of a few tens of microns, the selected elementary detectors then have a smaller size than this value.

The detector may be a gas microsensor. By microsensor is meant a sensor with a useful surface area of about 100 nm² to a few μm² along the diameter of the column. The microsensor is preferably integrated to the internal wall of the column. Preferably, the detectors are as small as possible, which allows an increase in the sensitivity of the detection means. This is in particular the case of NEMS sensors, for which at least one of the side dimensions is less than one micron. It is even possible to produce an elementary detector with several juxtaposed NEMS sensors. Any type of sensor, for which the size is less than a few tens of microns may be suitable. This is for example the case of sensors based on chemically functionalized nanostructures, such as for example carbon nanotubes or silicon nanowires.

During the passing of a gas species in proximity to the detector, molecules interact with the detector, this interaction producing a detectable electric signal.

These detectors advantageously have relative selectivity. Selectivity for example stems from a sensitive polymeric layer deposited on the sensor. This polymer may either be identical or not to the stationary phase. Alternatively, functionalization of the detectors in the column with several different sensitive polymers may be contemplated.

These may be gravimetric NEMS nanosensors. This type of sensor has a vibrating surface on which a gas species migrating in the column is deposited. Depositing this species induces a change in the resonance frequency, which may be measured for example by a capacitive or piezoelectric or piezoresistive effect. As a reminder, within the scope of capacitive detection, two electrodes are made for which the spacing between them varies with the movement of the mobile portion of the NEMS, including the change in the capacitance formed by both electrodes. For piezoelectric and piezoresistive detections, a strain gauge is made in a suitable material, for which the electric voltage on the terminals or the resistance respectively vary depending on the stress applied to the gauge.

NEMS detectors are for example gravimetric NEMS sensors such as those described in document Whiting, J. J., C. S. Fix, J. M. Anderson, et al. "*High-speed two-dimensional gas chromatography using microfabricated GC columns combined with nanoelectromechanical mass sensors*" in *TRANSDUCERS 2009—15th International Conference on Solid-State Sensors, Actuators and Microsystems*, 2009.

The gravimetric sensor is for example in SiN, and has the following dimensions 2.5 μm×0.7 μm.

The sensors are advantageously functionalized with a sensitive polymer, or any other adsorbing material having chemical affinity with the compound of the mixture to be analyzed. In the presence of a chemical compound, a certain amount of this compound will be adsorbed on the sensitive layer and will generate a signal on the sensor. The adsorbing material may be identical with the stationary phase or be different therefrom.

Obviously, it is understood that an elementary detector may be formed with several NEMS microsensors.

These may also be other known gas microsensors or nanosensors: notably conductimetric sensors, the deposit of molecules on a support then being accompanied by a change in conductivity. The support may consist of carbon nanotubes.

These may also be thermo conductivity detectors (TCD). They can be manufactured on silicon chips as in Kaanta, B., H. Chen, and X. Zhang, *A monolithically fabricated gas chromatography separation column with an integrated high sensitivity thermal conductivity detector*. Journal of Micromechanics and Microengineering, 2010, 20(5): p. 055016.

However, this kind of detector has the following drawbacks:

the discrimination of different analytes is comparatively very poor since it is only based on the conductivity of the vapour, which is, on the first order only a function of its molecular weight. The discrimination of two analytes with close molecular weight and different polarity will be possible with an adsorption on a sensitive polymer, but not with a TCD;

the signal delivered by a TCD detector depends on the velocity of the carrier gaz. It is thus important to keep a very good control of the velocity.

with TCDs, a stronger signal is obtained by increasing the difference between the thermal conductivity of the analytes and the carrier gas. As a consequence, hydrogen or helium are commonly used. Those two gases are either explosive or expensive.

Although TCDs can be used, affinity based detectors as chemiresistors or electromechanical systems (MEMS or NEMS) are preferably chosen for the following reasons:

they are much less sensitive to the velocity of the gas carrier, they are selective according to physi/chemical properties of the analyte (polarity, polarisability, presence of specific chemical functions, etc).

In this case, even if the separation by the chromatography column is not perfect, combining several detectors with different and complementary chemical layers makes still possible to discriminate a few analytes that would not be separated. Such an arrangement makes it possible to analyse more complex mixtures (i.e. with more compounds). Different analytes will give different signal patterns.

Figure 9:
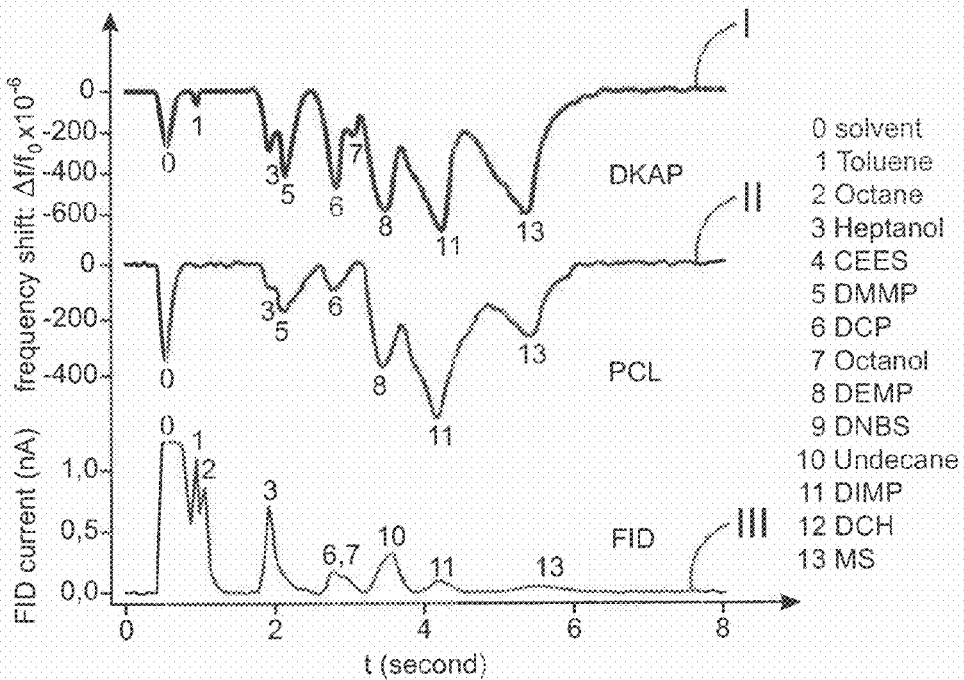
FIG. 9 is an example of curves delivered by analysis system according to the invention, curves I and II corresponding to systems having different stationary phases, and curve II corresponding to analysis made by a Flame ionization Detector.

For example in FIG. 9, the curves I and II are signals delivered by NEMS that are functionnalized with different polymers (respectively PCL that is polycaprolactone and DKAP that is a poly[(2-(3-propyl)-3,5-bis(trifluoromethyl) phenol]methyl)siloxane). We can see on this curve that the two polymers give different responses. It is particular clear for example for peaks number 1 which corresponds to toluene), 3 which corresponds to heptanol, and 7 which corresponds to octanol which shows better response with DKAP polymer.

The curve III is the response of a Flame Ionization Detector (FID), which is a reference detector for the gas chromatography installations. It can be seen when comparing curve I or II and curve III the performance of the system of the invention.

The other detected picks correspond to:
0: solvent
2: octane
4: CEES (2-Chloroethyl ethyl sulfide)
5: DMMP (dimethyl methylphosphonate)
6: DCP (diethyl chlorophosphate)
8: DEMP (diethyl methylphosphonate)
9: DNBS (di-n-butyl sulfide)
10: Undecane
11: DIMP (diisopropyl methylphosponate)
12: DCH (dichlorohexane)
13 MS: methyl salicylate.

The solvent is dietly ether. To make the chronograms of FIG. 9, all the analytes were dissolved in diethyl eter to produce a masse concentration of 0.5%.

Figure 2A:
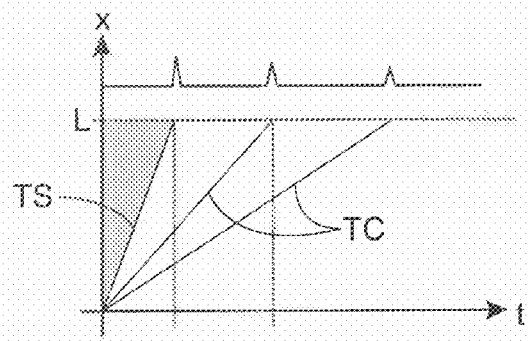

As indicated above, by means of the invention, it is possible to determine the average velocity of each compound between two successive detectors, a possibly variable velocity depending on the position of the compound in the column. It is then possible to reconstruct a two-dimensional space-time concentration map of the compounds in the column, as illustrated in FIG. 2A. In FIG. 2A, the axis of abscissas represent time t and the axis of ordinates represents the distance x covered in the column. This map is obtained in the case when the stationary phase has uniform characteristics along the column, i.e. the velocities of the compounds are then substantially constant. The characteristics of the stationary phase are for example the composition of the surface, its thickness, its temperature, etc. In FIG. 2A, the trajectory TS of the solvent and the trajectories TC of two constituents contained in the sample may be seen.

Thus, a point (x, t) of this map is the gas concentration detected by the detector in position x at instant t. A chromatogram obtained by a system of the state of the art would be in this map the straight line of equation x=L, L being the length of the column, the single detector being located at the column outlet. A straight line t=t0 of this map represents the position of the compounds along the column at instant t0. In such a map, the trajectory of an analyte is a line segment TC, assuming that the characteristics of the stationary phase are constant throughout the column. The slope of a line corresponds to the velocity of the compound in the column. With the velocity, it is then possible to characterize the compound in the column.

In the case when the thickness of the stationary phase varies along the column, the transit velocities of each of the compounds in the column vary in the same direction, i.e. either the velocities decrease or they increase, which ensures that the compounds do not mix together again.

In the case when the composition of the stationary phase varies along the column, the transit velocities of each of the constituents in the column may vary differently from each other, so that the constituents may pass each other. Such a configuration is impossible to process with the devices of the prior art. Now, by means of the present invention, it is possible to compensate for a variation of composition.

Figure 2B:
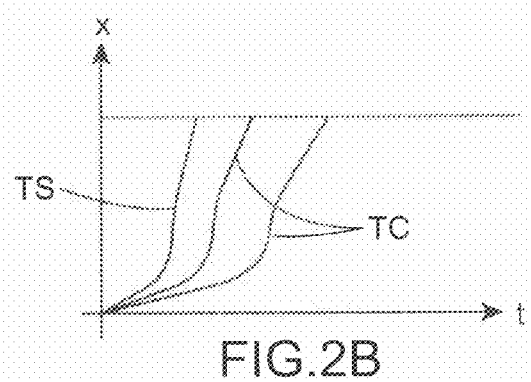

In FIG. 2B, a two-dimensional space-time concentration map may be seen for compounds in the column in the case when the stationary phase does not have uniform characteristics along the column; the velocities of the compounds then locally vary during their displacement in the column. As this may be seen, the trajectories of each of the compounds TC are curves. It should be noted that the trajectory designated as TS is that of the solvent.

Figure 3:
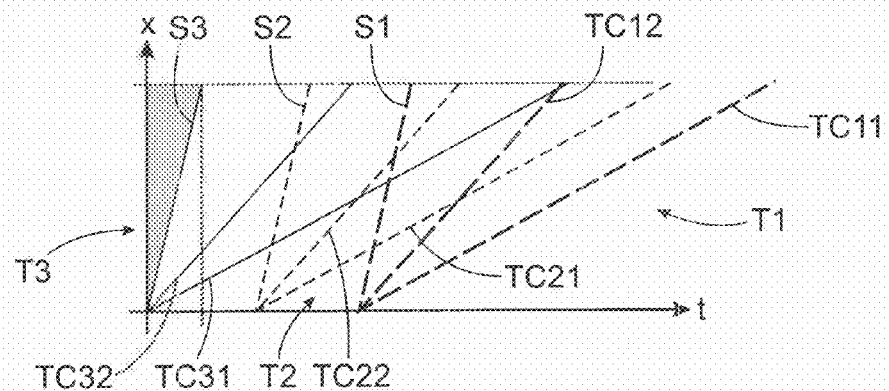

By means of the present invention, it is possible to carry out analyses with a higher rate than in the state of the art. Indeed, it is no longer necessary to wait for all the compounds of a previous sample to exit the column before injecting a next sample, since each of the compounds is tracked during its displacement in the column and is no longer only detected at the outlet. This is particularly visible on the map of FIG. 3. The relevant column has a stationary phase, the characteristics of which do not vary. The bundle of trajectories T1 illustrated in long dashed lines corresponds to the last injected sample, the bundle of trajectories T2 in short dashed lines corresponds to the second injected sample and the bundle of trajectories T3 in solid lines corresponds to the first injected sample.

Each bundle includes the trajectory of the solvent S, and two trajectories of two compounds C1, C2.

The bundle T1 includes the trajectories S1, TC11, TC12.
The bundle T2 includes the trajectories S2, TC21, TC22.
The bundle T3 includes the trajectories S3, TC31, TC32.

As illustrated on the map, the compound T2 moves more rapidly than the compound T31 and "overtakes" it in the column. Now, this does not perturb the analysis since, by means of the map, this "overtaking" is clearly localized. Each compound of each sample is therefore clearly distinguished and it is always known to which compound of which sample corresponds a peak.

Therefore, by means of the invention, the injection time between two samples may be less than the transport time of the last gas constituent.

It is therefore possible to carry out analyses more rapidly.

Figure 4A:
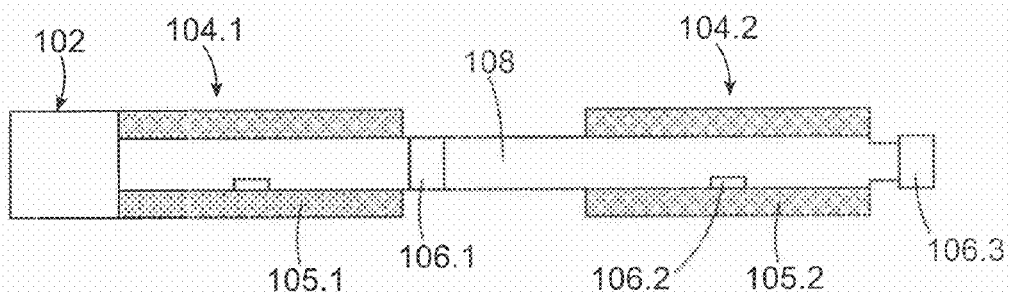

In FIG. 4A, another example of an analysis system S100 according to the present invention may be seen, including two chromatography columns 104.1, 104.2 connected in series. Both columns 104.1, 104.2 include different stationary phases 105.1, 105.2. In the relevant example, both columns have stationary phases, the characteristics of which do not vary.

The system includes an injection means 102 upstream from the first column 104.1, and detection means 106. In the illustrated example, both columns 104.1, 104.2 are connected through an intermediate area 108, the composition of which is not necessarily monitored.

According to the present invention, the detection means 106 ensure detection in several locations of the first 104.1 and second 104.2 columns and also in the intermediate area 108.

The detection means 106, in the illustrated example, include a detector at the outlet 106.1 of the first column 104.1, a detector 106.2 in the second column 104.2 and a detector 106.3 at the outlet of the second column 104.2. The first column 104.1 has a length L1, the second column has a length L2 and the intermediate portion 108 has a length L3.

Figure 4B:
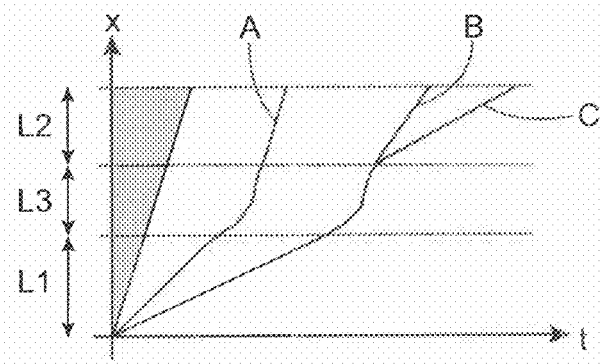

In FIG. 4B, the map of the trajectories obtained by means of the system of FIG. 4A may be seen for a sample including three compounds A, B and C.

The columns 104.1, 104.2 and the intermediate area 108 are illustrated on the map by three horizontal bands.

A sample including three compounds A, B and C is introduced into the analysis system of FIG. 4A. The first column 104.1 separates the compound A from the two other compounds B and C, the latter not being separated in this first column. In the second column 104.2, the compounds B and C are separated.

By analyzing the trajectories in both columns 104.1, 104.2, it is possible to estimate the transit velocities of each of the three compounds in both columns. Qualitatively, it is seen that:

compound A is moderately retained in the first area and very little in the second,
compounds B and C are retained in an identical way in the first area, in a more significant way than for A,
B is relatively not very retained in the second column, but however more than A, and
C is significantly retained in the second column.

Figure 4C:
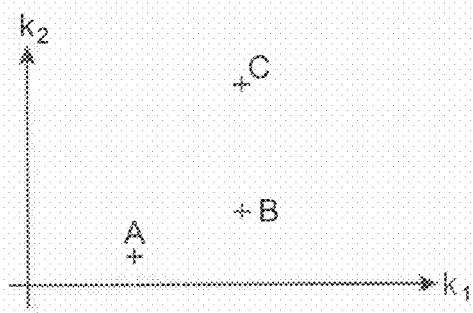

In FIG. 4C, the corresponding chromatography map may be seen, having in abscissa the retention coefficient k1 of the first column 104.1 and in ordinate the retention coefficient k2 of the second column 104.2.

By means of the invention, the compounds may be tracked during all their displacements in the columns, it is no longer necessary to modulate the flow rates in order to avoid that certain compounds "overtake" other compounds during their displacement in the successive columns.

The intermediate area is not involved in the separation; however its presence between both columns is not detrimental to the performance of the detection system. Obviously, it is understood that two columns may be connected in series without any intermediate area.

Figure 5A:
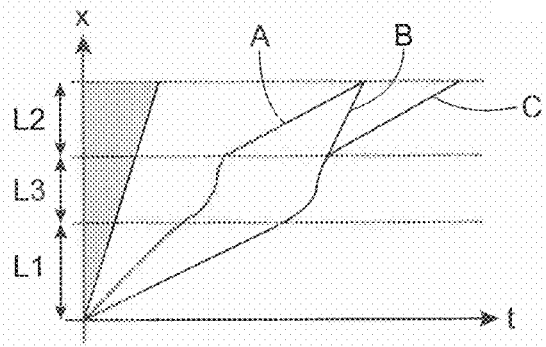

In FIG. 5A, a map of trajectories obtained with an analysis system similar to the one of FIG. 4A may be seen for a sample, the compounds of which have different affinities with the stationary phases.

A sample of three compounds A, B and C is introduced into the system S100. In this example, the compounds B and C are not separated by the first column 104.1. The second column 104.2 is such that the compound B "catches up" with the compound A so that it does not form any distinct peak at the outlet of the second column 104.2. However in this case, by means of the present invention, the detectors in particular located along the second columns 104.2 according to the present invention allow the trajectories of the compounds A and B to be distinguished.

The analysis of the trajectories in both columns 104.1, 104.2, allows an estimation of the transit velocities of each of the three compounds in both columns:

compound A is moderately retained in the first column and more significantly in the second column,
compounds B and C are retained in an identical way, in the first column, in a more significant way than for A,
B is not much retained in the second column, and
compound C is significantly retained in the second column, substantially the same as with A.

Figure 5B:
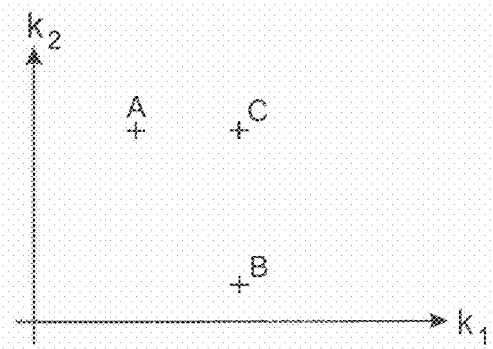

In FIG. 5B, the corresponding chromatography map may be seen, with in abscissa the retention coefficient k1 of the first column 104.1 and in ordinate the retention coefficient k2 of the second column 104.2.

Obviously, it is understood that systems of columns connected in series, in which the characteristics of stationary phases vary, do not depart from the scope of the present invention.

In the illustrated example, two columns are connected in series, however by means of the invention, any number of columns, greater than two, may be connected together, in order to increase the capabilities of separation of the analysis system. Thus, by means of the invention and in a more general way, by arranging a plurality of columns or column segments connected in series Cj, with $1 \leq j \leq N$ and $N \geq 2$, the columns following the first column, i.e. those with an index from 2 to N, having one or more detectors inside the column, in a sufficient number for determining the trajectories of each of the components, and possibly of a detector at the outlet. Preferentially, N is comprised between 2 and 7.

The first column may not include any detector or only include a single detector at the outlet.

For a solute Ri and for each column Cj, an average velocity $VR_{i,j}$ is determined.

To each solute Ri corresponds a point of an N-dimensional space, each axis j representing the velocity V determined in the column j. In other words, the solute Ri has in this space, coordinates (VRi,1 ... VRi,N). In an analogous way, to each solute corresponds a point of an N-dimensional space, each axis j representing the retention coefficient in column j. Each solute Ri then has coordinates (KRi,1, ... KRi,N) in this space, each coefficient KRi,j representing the retention coefficient in column j.

Figure 6A:
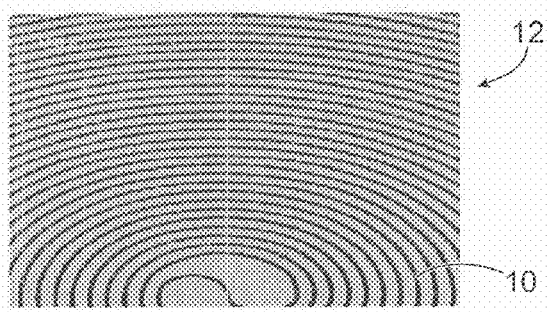
Figure 6B:
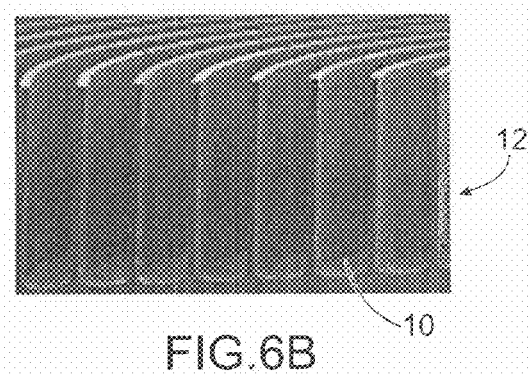

In FIGS. 6A and 6B, an exemplary embodiment of a chromatography column 4 in the form of two spirals wound into each other is illustrated as seen from the top and in a longitudinal sectional view.

This column is made by etching a groove 10 in a planar substrate 12, for example of silicon, by standard microelectronic techniques associating photolithographic and deep etching steps.

On a surface area of a few square centimeters, a column may thereby be made:
- the section of which is determined by the etching depth and the width of the etching. Each of these dimensions may vary from about ten to a few hundred microns,
- the length of which may range from a few tens of centimeters to one or several meters, for example two meters.

The groove 10 may also be a square spiral or a more complex shape (see example 1).

In FIGS. 7, 8A and 8B, another exemplary column 4 may be seen, the groove 10 of which includes parallel forward 14.1 and backward 14.2 sections etched in a substrate 12.

The groove 10 etched in a substrate 12, for example in silicon, is closed by a plate 16 forming a cover as illustrated in FIGS. 8A and 8B, this plate 16 is for example made in silicon, in silica or in Pyrex®. Attachment of the cover over the substrate is obtained by a known method of standard microelectronics, for example by molecular sealing or anodic sealing. Adhesively bonding the cover onto the substrate by means of an adhesive deposited by screen-printing may also be contemplated.

In this exemplary embodiment, the sensors are made on the face of the cover 16 intended to face the groove 10. The sensors 6 are then deposited according to a pattern corresponding to the shape of the groove 10 in the substrate 12.

In another exemplary embodiment, provision is made for making the sensors 6 directly in the groove before setting the lid into place.

As regards the deposition of the stationary phase and that of the polymer on the sensors, these depositions may take place before the assembling or after the assembling. In the case when the polymers of the stationary phase and of the sensors are the same, deposition after assembling allows both of these depositions to be carried out simultaneously.

For making a system including columns connected in series, for which the stationary phases are different, the depositions may take place before or after setting the cover into place.

As an example, a system according to the present invention may be made according to the following method. The system includes three modules each made in a different substrate:
- the gas phase chromatography module including the column(s) is made by deep silicon-etching in a first substrate,
- the detection module comprising the detection means is made as a network of NEMS sensors obtained by photolithography and etching on a second substrate, the position and shape of which correspond to the groove cut in the first substrate,
- the electronic module for controlling and processing the data delivered by the NEMS sensors is made as a network of ASIC (Application-Specific Integrated Circuit) integrated circuits implemented in CMOS technology on a third substrate.

These three substrates are assembled by superposing them, thereby making a structure by stacking three substrates.

For example, the assembling of the first and second substrates is achieved by adhesion, for example by adhesive bonding or any other sealing method used in microtechnology. Chemical functionalization of the column(s) and of the detectors by depositing polymer may be performed on each of the substrates separately before assembly or on the whole set after assembly. Assembling the third substrate with the assembly formed by the first and second substrates is for example achieved by means of mechanical attachment accompanied with an electric connection between each of the detectors and an ASIC integrated processing circuit.

Figure 10:
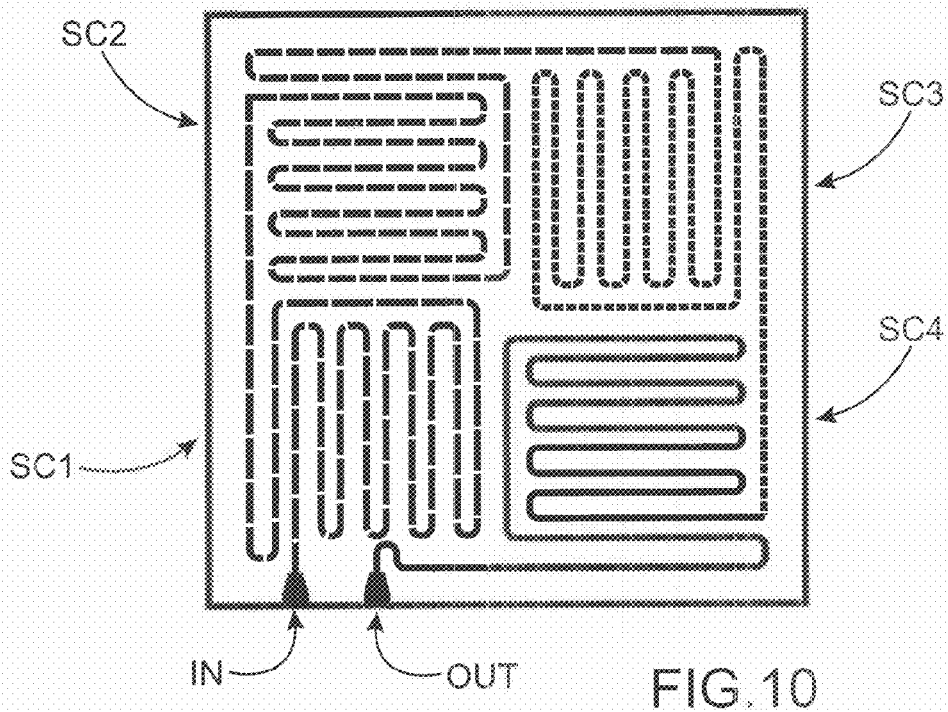
FIG. 10 is a schematic illustration of a another embodiment of a analysis system of the invention.
Figure 11:
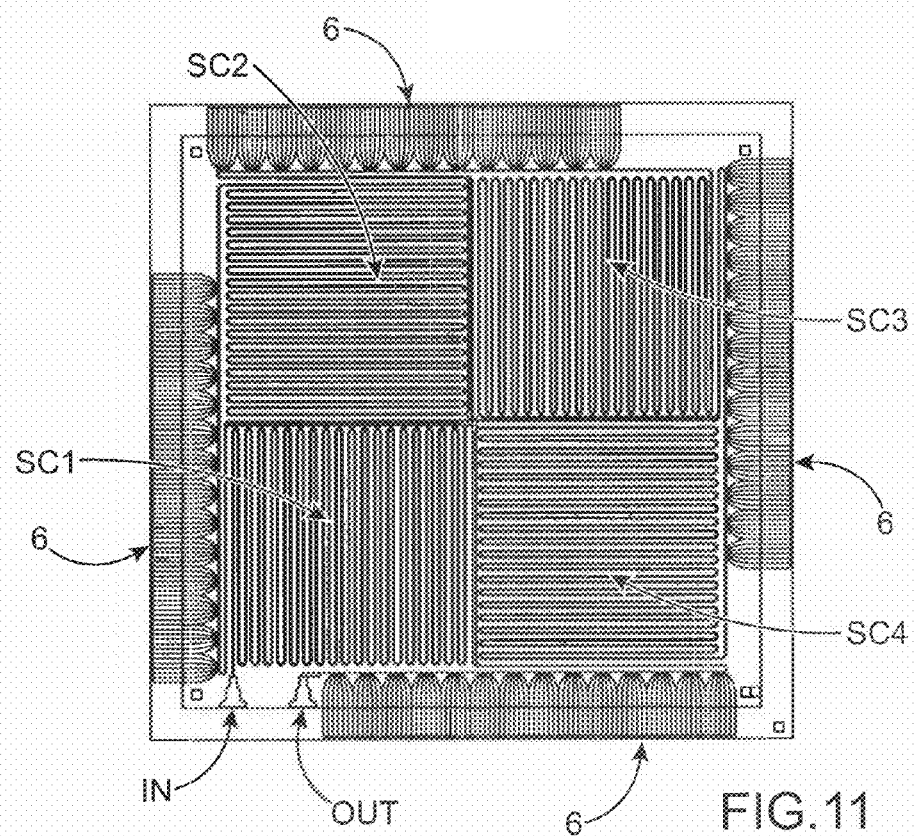
FIG. 11 is a representation of an example of a precise layout of the system of FIG. 10.

FIGS. 10 and 11 depict a particular design of a gas chromatography column which is especially adapted when we have four groups of detectors that are conveniently spread along the whole length of the column.

FIG. 10 is a schematic representation of the gas chromatography column. This particular column is composed of four sub-columns SC1, SC2, SC3, SC4, which form each one a quarter of the complete column. The precise layout of the column is shown on FIG. 11.

Figure 12:
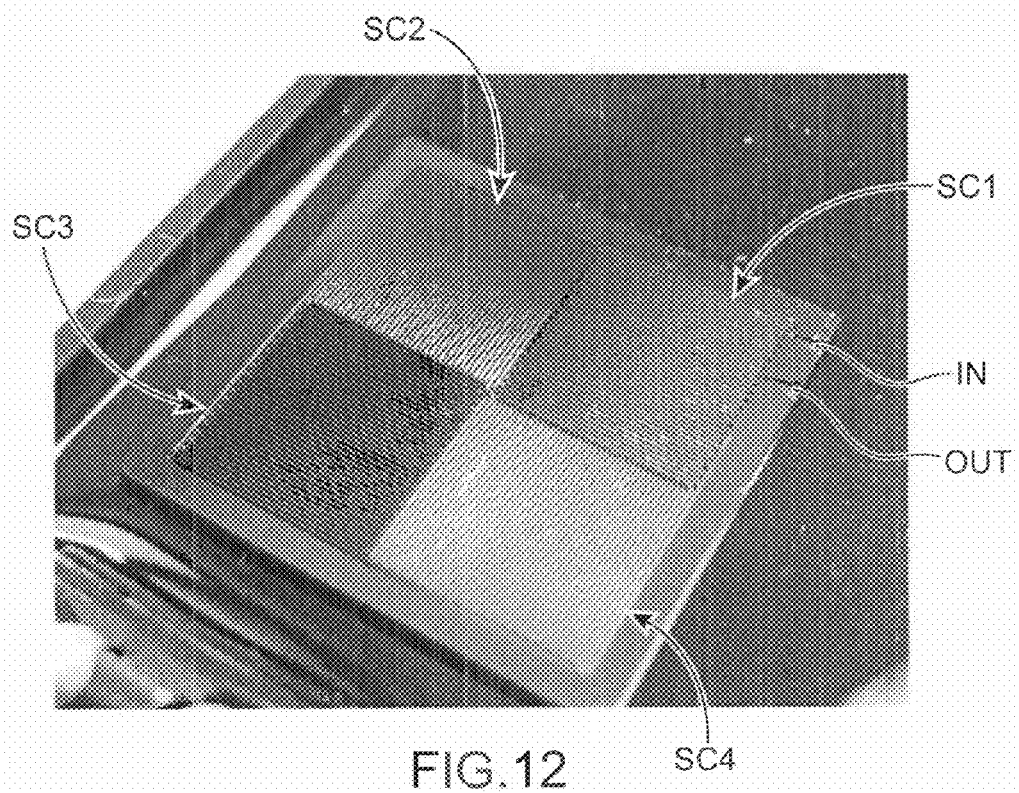
FIG. 12 is photography of an actual system according FIG. 11.

FIG. 12 is a picture of the actual device that is manufactured.

The four sub-columns SC1, SC2, SC3, SC4 have an identical shape and length, with the minor exception of the extremity ones. Those ones have a little difference to arrange the inlet IN and outlet OUT of the whole column. The design of the column is such that it can located on a detectors plane with detectors 6 on the periphery of this plane. A group of NEMS detectors 6 (exactly 14 detectors in each group in this particular design) is located on each of the four sides of the detectors plane and close to the edge. The location of the detectors along the edges of the detectors plane, makes their connection to the readout electronics easier by minimizing the length of the electrical leads. Besides the design offers a large length on the periphery to mount the detectors along each sub-column.

The particular shape of the column allows each group of detectors to be located evenly along the column, respectively after the first, second, third and last quarter of the column.

This particular design makes it easier to coat the different sub-columns with different stationary phases. The whole column can then be functionalized easily with one to four different stationary phases, in order to perform multi-dimensional gas chromatography.

The invention claimed is:

1. A system for analyzing a gas mixture, comprising:
at least one chromatography column comprising at least one inlet and at least one outlet, at least one wall having an inner surface extending from the at least one inlet to the at least one outlet, and a film of at least one stationary phase covering the inner surface;
at least one injector configured to inject the gas mixture into the at least one chromatography column; and
a detection system comprising a plurality of detectors integrated in the at least one wall and disposed in at least two locations inside the at least one chromatography column along a length taken between and including the inlet and the outlet, the detection system being configured to detect at least one compound included in the gas mixture in the at least two locations.

2. The analysis system according to claim 1, wherein the plurality of detectors are functionalized by depositing a layer of adsorbing material on at least one surface thereof.

3. The analysis system according to claim 2, wherein the adsorbing material is identical with that of the film of the stationary phase.

4. The analysis system according to claim 1, wherein a spacing between two consecutive detectors of the plurality of detectors is less than or equal to a half-width of a peak, an average value of the peak being estimated from a height equivalent of a theoretical plate (HETP).

5. The analysis system according to claim 4, wherein the spacing between the two consecutive detectors is about 1 mm.

6. The analysis system according to claim 1, wherein the detectors are gravimetric sensors.

7. The analysis system according to claim 1,
wherein the at least one chromatography column is of a microcapillary type or a macrocapillary type, and
wherein the detectors are nanoelectromechanical (NEMS) sensors or microelectromechanical (MEMS) sensors.

8. The analysis system according to claim 7, wherein the detectors have a sensing surface area between about 100 $nm^2$ and about a few $\mu m^2$.

9. The analysis system according to claim 1,
wherein the at least one chromatography column includes at least a first chromatography column and at least a second chromatography column connected in series, and
wherein the detection system is associated with each of said at least the first chromatography column and said at least the second chromatography column.

10. The analysis system according to claim 1, wherein the at least one chromatography column comprises an etched groove in a substrate, the groove being closed with a plate.

11. The analysis system according to claim 10, wherein the plurality of detectors are disposed in the groove or on the plate according to a pattern corresponding to a shape of the groove.

12. The analysis system according to claim 11,
wherein a shape of the at least one chromatography column is arranged to have at least a portion of the at least one chromatography column located along at least one edge of the substrate, and
wherein the detection system is located next to the at least one edge of the substrate.

13. The analysis system according to claim 12, wherein the at least one chromatography column comprises four parts connected to each other, each part having a serpentine shape, a portion of each serpentine shape being located along a different edge of the at least one edge of the substrate.

14. The analysis system according to claim 13, wherein the four parts have a same length.

15. The analysis system according to claim 14, wherein the four parts are coated with different stationary phases.

16. A method for analyzing a plurality of samples of a gas mixture using a system according to claim 1, comprising:
injecting each of the plurality of the samples into the at least one chromatography column successively;
detecting at least one peak corresponding to the at least one compound included in the samples;
establishing at least one map of at least one trajectory corresponding to the at least one compound; and
determining a local velocity of each of the plurality of the samples between two successive detectors of the plurality of detectors in the at least two locations.

17. The method according to claim 16,
wherein a first time between two of the successive injections is less than a second time for transporting a slowest constituent of the first injection, and is less than a third time for transporting a gas solvent.

\* \* \* \* \*